US006420626B1

(12) United States Patent
Erspamer et al.

(10) Patent No.: US 6,420,626 B1
(45) Date of Patent: Jul. 16, 2002

(54) UNITARY FLUID ACQUISITION, STORAGE, AND WICKING MATERIAL

(75) Inventors: John P. Erspamer, Bartlett, TN (US); Shiu-Kang Laurence Li, Delta (CA); James Richard Gross, Cordova; Samuel Charles Baer, Germantown, both of TN (US)

(73) Assignee: Buckeye Technologies Inc., Memphis, TN (US)

( * ) Notice: Subject to any disclaimer, the term of this patent is extended or adjusted under 35 U.S.C. 154(b) by 0 days.

(21) Appl. No.: 09/325,764

(22) Filed: Jun. 8, 1999

(51) Int. Cl.[7] ................................................. A61F 13/15
(52) U.S. Cl. ....................... 604/378; 604/383; 604/367; 604/365; 428/131; 428/137
(58) Field of Search ................................ 604/370, 378, 604/385.01, 385.23, 365, 367, 383; 428/131–140, 170–172

(56) References Cited

U.S. PATENT DOCUMENTS

| 4,699,619 | A | * | 10/1987 | Bernardin | .................. 604/378 |
|---|---|---|---|---|---|
| 5,288,348 | A | | 2/1994 | Modrak | ..................... 156/62.2 |
| 5,549,589 | A | * | 8/1996 | Horney et al. | .............. 604/366 |
| 5,569,226 | A | | 10/1996 | Cohen et al. | ................ 604/378 |
| 5,593,401 | A | * | 1/1997 | Sosalla et al. | ........... 604/385.2 |
| 5,607,414 | A | * | 3/1997 | Richards et al. | ............. 604/378 |
| 5,653,702 | A | | 8/1997 | Brohammer et al. | ........ 604/370 |
| 5,873,869 | A | | 2/1999 | Hammons et al. | ....... 604/386.1 |
| 5,879,343 | A | | 3/1999 | Dodge, II et al. | .......... 604/378 |
| 5,885,268 | A | | 3/1999 | Bien et al. | ................ 604/385.1 |
| 5,891,120 | A | * | 4/1999 | Chmielewski | .............. 604/378 |
| 5,954,705 | A | * | 9/1999 | Sawaki et al. | ............ 604/385.1 |
| 6,037,518 | A | * | 3/2000 | Guidotti et al. | ............. 604/378 |
| 6,103,953 | A | * | 8/2000 | Cree et al. | ................... 604/365 |
| 6,107,537 | A | * | 8/2000 | Elder et al. | .................. 604/364 |

* cited by examiner

*Primary Examiner*—John G. Weiss
*Assistant Examiner*—Jacqueline Stephens
(74) *Attorney, Agent, or Firm*—Darby & Darby

(57) ABSTRACT

Disclosed is a unitary absorbent structure including a fluid acquisition stratum; a fluid distribution stratum; and a fluid storage stratum between the acquisition stratum and the distribution stratum. Each of the acquisition, distribution, and storage strata are in fluid communication with each other.

19 Claims, 1 Drawing Sheet

UNITARY FLUID ACQUISITION, STORAGE, AND WICKING MATERIAL

FIELD OF THE INVENTION

The present invention is directed to improved fibrous absorbent structures having separate layers (or strata) as regions for fluid acquisition, storage, and distribution. The structures are useful in providing improved disposable absorbent products, such as diapers, adult incontinence pads, and sanitary napkins.

BACKGROUND OF THE INVENTION

Absorbent articles such as disposable diapers, adult incontinence pads, sanitary napkins, and the like, are generally provided with an absorbent core or storage layer, to receive and retain bodily liquids. The absorbent core is usually sandwiched between a liquid previous top sheet, whose function is to allow the passage of fluid to the core, and a liquid impervious backsheet which contains the fluid and prevents it from passing through the absorbent article. An absorbent core (e.g., for diapers and adult incontinence pads) typically includes fibrous batts or webs constructed of defiberized, loose, fluffed, hydrophilic, cellulosic fibers. The core may also include superabsorbent polymer (SAP) particles, granules, flakes or fibers. In addition, an absorbent article may contain a distribution layer that aids in transporting liquid quickly from the acquisition layer to the storage layer of the core. Conventional absorbent products have used separately formed layers for acquisition, distribution, and storage leading to complex and crowded production lines. A need, therefore, exists for an absorbent product where the acquisition, distribution, and storage functions are all performed in a single integrated structure.

Market demand for thinner and more comfortable absorbent articles has increased. Such articles may be obtained by decreasing the thickness of the diaper core, by reducing the amount of fibrous material used in the core while increasing the amount of SAP particles, and by calendering or compressing the core to reduce caliper and hence, increase density. However, higher density cores do not absorb liquid as rapidly as lower density cores because densification of the core results in smaller effective pore size. Accordingly, to maintain a suitable liquid absorption rate, it is necessary to provide a lower density layer having a larger pore size above the high density absorbent core to increase the rate of acquisition of liquid discharged onto the absorbent article. Because of the inadequate pore sizes, traditional absorbent structures have suffered from an inability to absorb large surges of fluid. A need clearly exists for absorbent structures having an acquisition layer of sufficient pore size to better accommodate fluid surges.

In a conventional multilayer absorbent structure having an acquisition layer, a distribution layer and a storage layer, the acquisition layer acquires the liquid insult and quickly transmits it by capillary action away from the skin of the wearer (in the Z-direction). Next, the fluid encounters the distribution layer. The distribution layer is typically of a higher density material, and causes the liquid to migrate away from the skin of the wearer (in the Z-direction) and also laterally across the structure (in the X-Y directions). Finally, the liquid migrates into the storage layer. The storage layer generally includes high density cellulosic fibers and SAP particles. The liquid is absorbed by the storage layer and especially the SAP particles contained therein.

Although the conventional multilayer structure described above can be effective, one disadvantage of this arrangement is that because the distribution layer is on the side of the storage layer facing the skin of the wearer, there is a possibility that liquid can pool against the skin of the wearer before it is absorbed by the storage layer due to relatively poor fluid retention of the distribution layer. As the wearer moves, pressure is created and can result in fluid being released, thereby rewetting the wearer. Accordingly, it would be desirable to provide a structure wherein liquid is immediately acquired and transmitted away from the skin of the wearer in the Z-direction; where it can be absorbed into the storage layer while minimizing or eliminating the problem of liquid recontacting the skin of the wearer.

SUMMARY OF THE INVENTION

The present invention provides a unitary absorbent structure including a fluid acquisition stratum; a fluid distribution stratum; and a fluid storage stratum between the acquisition stratum and the distribution stratum. Each of the acquisition, distribution, and storage strata are in fluid communication with each other.

DETAILED DESCRIPTION OF THE INVENTION

Figure 1:
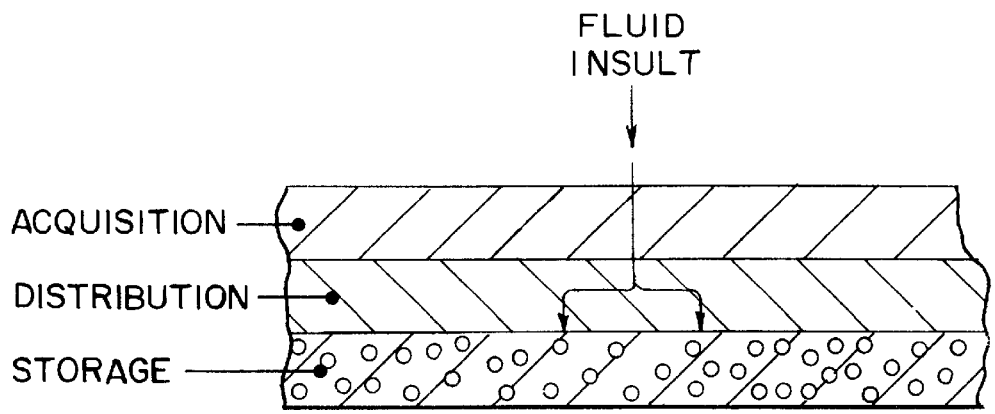
FIG. 1 shows a schematic cross section of a conventional multilayer absorbent structure.
Figure 2:
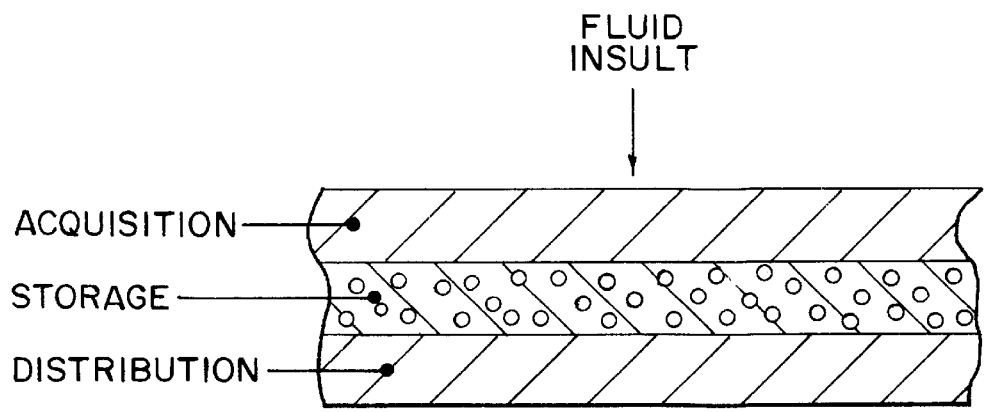
FIG. 2 shows a schematic cross section of one possible embodiment of the unitary multistrata absorbent structures of the invention.
Figure 3:
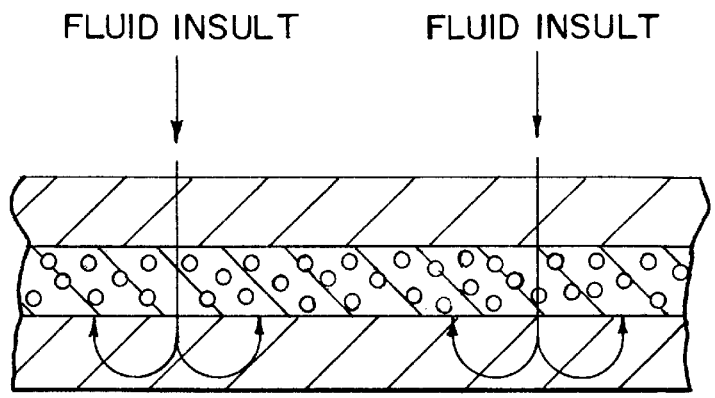
FIG. 3 shows a schematic cross section of the pathway of fluid absorption through the unitary multistrata absorbent structures of the invention.

All references cited in the subject application are fully incorporated by reference. In case of inconsistencies, the present description, including definitions, is intended to control.

The present invention includes a unitary, multi-zone or multi-strata absorbent structure having an acquisition stratum which acquires the liquid insult and quickly transmits it by capillary action away from the skin of the wearer (in the Z-direction); a storage stratum containing higher density matrix fibers and SAP particles; and a distribution stratum which absorbs and retains some of the excess liquid passing through the storage stratum. As used herein, the terms "strata" and "stratum" refer to the layered regions which make up the unitary structure. The strata of the unitary structure is not an assembly or laminate of preformed layers forming a multilayered structure. Instead, the unitary structure is constructed by assembling the strata in a continuous, manner. Airlaid technology is the preferred method for assembling the strata of the unitary structure of the present invention.

In one embodiment, the distribution stratum includes a fibrous matrix material and causes the liquid to migrate laterally across the structure (in the X-Y directions) and back into the storage stratum, where the liquid is absorbed and retained by the SAP particles in the storage stratum. This arrangement causes liquid encountering the structure to be drawn away from the skin of the user and through the entire structure where it can be absorbed into the storage stratum with less propensity to pool or retain moisture at the interface of the structure and the skin of the wearer. This invention also includes an absorbent structure with an acquisition stratum having an increased pore size.

In a preferred embodiment, the absorbent structures of the present invention include at least three strata, all of which are in fluid communication with each other. These strata include: a fluid acquisition (upper) stratum, a fluid storage (middle) stratum, and a fluid distribution (lower) stratum.

The fluid acquisition (upper) stratum may include: polyester (i.e. PET) and/or synthetic homopolymer fibers; 0–10% SAP; and thermal or latex binder resin; and will typically have a basis weight of 20–120 gsm (grams per square meter). The fluid storage (middle) stratum may include: fluff cellulose and/or chemically modified cellulose fiber; 10–75% SAP; and thermal binder resin; and will typically have a basis weight of 60–400 gsm. The fluid distribution (lower) stratum may include: fluff cellulose and/or chemically modified cellulose fiber; 0–10% SAP; and thermal and/or latex binder resin; and will typically have a basis weight of 20–200 gsm.

A second preferred embodiment of this invention comprises four strata: a synthetic fiber acquisition stratum (top), a cellulosic fiber acquisition stratum (upper middle), a storage stratum (lower middle), and a distribution stratum (bottom).

The overall basis weight range of these composite structures are 100–720 gsm with an SAP content of 10–75%. The preferred basis weight range(s) and SAP content vary with the intended application. For feminine hygiene and light capacity adult incontinence applications, the basis weight and SAP content will tend toward the lower end of the ranges. For infant diaper and heavy capacity adult incontinence applications, the preferred basis weight and SAP content will tend toward the high end of the specified ranges.

The acquisition stratum is designed for minimum fluid retention. In a preferred embodiment, the matrix fiber(s) of the acquisition stratum is a synthetic fiber(s) that is at least 2 denier in size and capable of being latex bonded. Examples of suitable synthetic fibers include: polyesters, polyamides, and polyolefins, for example polyethylenes and polypropylenes. In another preferred embodiment, the acquisition stratum contains matrix fibers comprising 3 to 40 denier crimped PET fiber with a cut length of 3 to 12 mm.

The storage stratum is characterized by a relatively high concentration of superabsorbent polymer (SAP). The types of superabsorbent polymers which may be used in this invention include, for example: SAPs in their particulate form such as irregular granules, spherical particles, staple fibers and other elongated particles. U.S. Pat. No. 5,147,343; U.S. Pat. No. 5,378,528; U.S. Pat. No. 5,795,439; U.S. Pat. No. 5,807,916; and U.S. Pat. No. 5,849,211, describe various superabsorbent polymers and methods of making superabsorbent polymers. One example of a supeiabsorbent polymer forming system is crosslinked acrylic copolymers of metal salts of acrylic acid and acrylamide or other monomers such as 2-acrylamido-2-methylpropanesulfonic acid. Many conventional granular superabsorbent polymers are based on poly(acrylic acid) which has been crosslinked during polymerization with any of a number of multi-functional co-monomer crosslinking agents well-known in the art. Examples of multi-functional crosslinking agents are set forth in U.S. Pat. No. 2,929,154; U.S. Pat. No. 3,224,986; U.S. Pat. No. 3,332,909; and U.S. Pat. No. 4,076,673. For instance, crosslinked carboxylated polyelectrolytes may be used to form superabsorbent polymers. Other water-soluble polyelectrolyte polymers are known to be useful. for the preparation of superabsorbents by crosslinking, these polymers include: carboxymethyl starch, carboxymethyl cellulose, chitosan salts, gelatine salts etc. They are not, however, commonly used on a commercial scale to enhance absorbency of dispensable absorbent articles mainly due to their higher cost. Superabsorbent polymer granules useful in the practice of this invention are commercially available from a number of manufacturers, such as Dow Chemical (Midland, Mich.), Stockhausen (Greensboro, N.C.), and Chemdal (Arlington Heights, Ill.). In a preferred embodiment, the SAP is a surface crosslinked acrylic acid based powder such as Stockhausen 9350 or SX70.

Cellulose that has been modified to increase the degree of curl and stiffness of the individual fluff cellulose fibers (e.g. Buckeye HPF modified fluff cellulose) can be used in the storage stratum in place of or in addition to the standard fluff cellulose fibers to enhance the fluid acquisition and retention performance of the invention.

By distributing fluid in the x-y direction, the distribution stratum allows superabsorbent particles in the storage stratum that are far removed from the point of the fluid insult to absorb fluid. The distribution stratum also serves to pull fluid not immediately absorbed by the SAP of the storage stratum in the z-direction away from the wearer's skin.

The matrix fibers of the distribution stratum can include fluff pulp, modified fluff cellulose, or a blend thereof. In a preferred embodiment, the cellulosic fibers of the distribution stratum are modified to decrease the stiffness of the fibers, making the stratum more easily densified.

In a preferred embodiment of the invention, the fluid distribution stratum is comprised of primarily cellulosic fibers that have a mean pore size smaller than that of the fluid acquisition stratum and a pore size that is equal to or less than the pore size of the storage stratum. In general, a smaller mean pore size correlates with a higher density. Preferably, the density of the distribution stratum is greater than the density of the acquisition and storage strata. When the density of the distribution stratum is greater than the density of the acquisition stratum and storage stratum, a high fluid acquisition rate and low stain size factor of low density absorbent structures and the high fluid retention characteristic of high density structures can be achieved.

In a preferred embodiment, the strata of the claimed absorbent structures are formed as an airlaid web. Preferably, the absorbent strata are airlaid on top of a lightweight (i.e. 10–20 gsm) cellulose tissue or similar carrier layer that serves to contain the SAP powder during the web forming process and thus prevent plugging of the fiber collection wire with particles of SAP.

An airlaid web is typically prepared by disintegrating or fiberizing a cellulose pulp sheet or sheets, typically by hammermill, to provide individualized fibers. The individualized fibers are then air conveyed to forming heads on an airlaid web forming machine. Examples of several airlaid web forming machines are described in detail in U.S. Pat. No. 5,527,171 (Soerensen). The forming heads may include rotating or agitated drums which serve to maintain fiber separation until the fibers are pulled by a vacuum onto a foraminous condensing drum or foraminous forming conveyor (or forming wire). Other fibers, such as a synthetic thermoplastic fiber, may also be introduced to the forming head through a fiber dosing system which includes a fiber opener, a dosing unit and an air conveyor. Where two defined strata are desired, such as a fluff pulp distribution stratum and a synthetic fiber acquisition stratum, two separate forming heads may be used for each type of fiber. After the fibers are airlaid the resulting structure is densified and the fibers are bonded together.

Typically a calender is used to density the resulting structure. Compaction may also occur before all of the strata have been airlaid. For instance a first batt of airlaid fibers may be compacted to form a distribution stratum having a density of between about 0.08 and about 0.20 gr/cc prior to airlaying subsequent fiber batts.

The fibers of the acquisition, distribution, and/or storage strata may be bonded together by heat softening a thermoplastic binder present with the web fibers. The thermoplastic binder includes any thermoplastic polymer which can be melted at temperatures which will not extensively damage the cellulosic fibers. Preferably, the melting point of the thermoplastic binding material will be less than about 175° C. Examples of suitable thermoplastic materials include thermoplastic microfibers, thermoplastic powders, bonding fibers in staple form, and bicomponent staple fibers. In particular, the thermoplastic binding material may, for example, be polyethylene, polypropylene, polyvinylchloride, polyvinylidene chloride. Other synthetic fibrous materials which can be utilized in thermally bonded webs are described above. The thermoplastic binders may be intermixed with the cellulosic fibers in the airlaid web forming machine or may be added to the appropriate strata subsequent to their being airlaid.

Alternatively or in addition, the acquisition and distribution strata may be bonded together by applying a latex spray. Examples of elastomeric polymers available in latex form include butadiene-styrene, butadiene-acrylonitrile, and chloroprene (neoprene). Other examples of synthetic polymers that can be used used in latexes include polymers or copolymers of alkylacrylates, vinyl acetates such as ethylene vinyl acetate, and acrylics such as styrene-butadiene acrylic. For purposes of industrial hygiene and elimination of a solvent recycling step, the synthetic latexes can be applied as an aqueous based emulsion rather than an organic solvent emulsion. Latexes useful in the present invention may be prepared by emulsion polymerization of certain olefinic (ethylenically unsaturated) monomers. This emulsion polymerization can be carried out by customary methods using any of a variety anionic, nonionic, cationic, zwitterionic and/or amphoteric emulsifiers to stablize the resultant latex, including alkyl sulfates, alkylarylalkoxy sulfates, alkylarylsulfonates and alkali metal and/or ammonium salts of alkyl- and alkylaryl-polyglycol ether-sulfates; oxyethylated fatty alcohols or oxyethylated alkylphenols, as well as block copolymers of ethylene oxide and propylene oxide; cationic adducts of primary, secondary or tertiary fatty amines or fatty amine oxyethylates with organic or inorganic acids, and quaternary alkylammonium surfactants; and alkylamidopropylbetaines. The olefinic monomer can be a single type of monomer or can be a mixture of different olefinic monomers, i.e. to form copolymer particles dispersed or emulsified in the aqueous phase. Examples of olefinic monomers that can be used to form latex polymers include $C_2$-$C_4$ alkyl and hydroxy alkyl acrylates, such as those selected from the group of propyl acrylate, n-butyl acrylate, isobutyl acrylate, 2-hydroxyethyl acrylate, 2-hydroxypropyl acrylate, ethyl acrylate and mixtures thereof. Other examples are $C_1$-$C_4$ alkyl or hydroxy alkyl methacrylates selected from the group of propyl methacrylate, n-butyl methacrylate, isobutyl methacrylate, 2-hydroxyethyl methacrylate, 2-hydroxypropyl methacrylate, ethyl methacrylate, methyl methacrylate, vinyl acetate and mixtures thereof Also suitable are mixtures of the aforementioned $C_2$–$C_4$ alkyl and hydroxy alkyl acrylates and $C_1$–$C_4$ alkyl or hydroxy alkyl methacrylates. Methods of applying the latex include coating, dipping, brushing, spraying, and foaming. In a preferred embodiment, the latex is applied by spraying. The latex resin can be applied before or after compaction of the fiber web.

Bicomponent staple fibers are characterized by a high melt temperature core polymer (typically polyethylene terephthalate (PET) or polypropylene) surrounded by a low melt temperature sheath polymer (typically polyethylene (e.g., Hoechst-Trevira Type-255 (Charlotte, N.C.)), modified polyethylene, or copolyesters).

The bonded web may be calendered a second time to increase its strength or embossed with a design or pattern. If thermoplastic fibers are present, hot calendering may be employed to impart patterned bonding to the web. Water may be added to the web if necessary to maintain specified or desired moisture content, to minimize dusting, or to reduce the buildup of static electricity. The finished web is then rolled for future use.

The following examples are meant to illustrate the invention and not to limit its scope.

EXAMPLES

Examples of some preferred embodiments of the invention are described in Tables 1 and 2. The raw materials for the embodiments described in Tables 1, 2, and 3 are, unless otherwise noted:

| | |
|---|---|
| Fluff Cellulose: | Buckeye Foley Fluff (Buckeye Technologies Inc., Memphis, TN) |
| Bonding fiber: | Hoechst-Trevira T-255 from Hoechst-Trevira (Charlotte, NC) |
| Latex Binder: | AirFlex 192 from Air Products (Allentown PA) |
| PET fiber: | Type D2645 6 denier X 6 mm crimped fiber from Hoechst-Trevira (Germany) |
| Tissue: | 18 gsm (grams per square meter) wet laid |

Example 1

TABLE 1

Single Compaction Embodiment - Sample MJ998-MF-17

| | Fluff Cellulose (gsm) | Bonding Fiber (gsm) | SAP Powder (gsm) | Latex Binder Resin (gsm) | PET Fiber (gsm) |
|---|---|---|---|---|---|
| Acquisition Stratum | 0.0 | 0.0 | 0.0 | 6.0 | 34.0 |
| Storage Stratum | 55 | 5 | 40 | 0.0 | 0.0 |
| Distribution Stratum | 57 | 3 | 0.0 | 0.0 | 0.0 |

The MJ998-MF-17 material was formed on an M&J-type air forming line. The cellulosic distribution stratum was formed first onto a tissue. The storage stratum was then formed onto the distribution stratum and then the acquisition stratum was formed on top of the storage stratum. The resulting three strata material was thermal bonded and then compressed by calendering to achieve an overall density of 0.142 gr/cc.

Example 2

In an alternative embodiment, the distribution stratum is compacted first before the other strata are airlaid and all the strata are compacted together.

TABLE 2

Double Compaction Embodiment - Sample MJ998-MF-18b

|  | Fluff Cellulose (gsm) | Bonding Fiber (gsm) | SAP Powder (gsm) | Latex Binder Resin (gsm) | PET Fiber (gsm) |
|---|---|---|---|---|---|
| Acquisition Stratum | 0.0 | 0.0 | 0.0 | 6.0 | 34.0 |
| Storage Stratum | 55 | 5 | 40 | 0.0 | 0.0 |
| Distribution Stratum | 57 | 3 | 0.0 | 0.0 | 0.0 |

The MJ998-F-18b material was formed on an M&J-type air forming line. The cellulosic distribution stratum was formed on tissue and compacted by calendering to a density of 0.15 gr/cc. The storage stratum was then formed onto the distribution strata and then the acquisition stratum was formed on top of the storage stratum. The resulting three strata material was compacted and then thermal bonded to achieve an overall composite material density of 0.081 gr/cc.

Example 3

It is preferred that the cellulose fibers of the distribution stratum be thermally bonded together. Table 3 describes a composite example where a thermal bonded fluff cellulose distribution stratum resides above the storage stratum and below the acquisition stratum.

TABLE 3

Absorbent Structure with Distribution Stratum Above Storage Stratum - Sample MJ998-MF-9 (Reference)

|  | Fluff Cellulose (gsm) | Bonding Fiber (gsm) | SAP Powder (gsm) | Latex Binder Resin (gsm) | PET Fiber (gsm) |
|---|---|---|---|---|---|
| Acquisition Stratum | 0.0 | 0.0 | 0.0 | 6.0 | 34.0 |
| Distribution Stratum | 57 | 3 | 0.0 | 0.0 | 0.0 |
| Storage Stratum | 55 | 5 | 40 | 0.0 | 0.0 |

The MJ998-MF-9 material was also formed on an M&J-type pilot line. This material reflects a previously described construction in that the fluid storage stratum is formed first. The distribution stratum is formed on top of the storage stratum and then the acquisition stratum is formed on top of the distribution stratum. The fluff cellulose in the distribution stratum was Buckeye HPF fiber. This three strata structure was thermally bonded and compacted to achieve an overall density of 0.094 gr/cc.

Fluid, Acquisition and Fluid Retention Testing

The composite materials described above were subjected to fluid acquisition testing. Each sample (having the dimensions of 10 cm×25cm) was wrapped with an appropriate coverstock material and placed on a bottom fluid intake test ("FIT") board with the wire or carrier side facing down. The center of the samples was marked.

Acquisition rate evaluations were made by subjecting test samples to three consecutive 10 ml insults of 0.9% saline solution. The first insult of 1.0 ml 0.9% saline solution was poured into the clear addition tube of the FIT board as fast as possible, without overflowing. The time from the moment of pouring until the saline reached the test sample was measured. The stopwatch was stopped as soon as all of the saline passed from the bottom edge of the tube. The recorded time was the time required for acquisition by the top stratum. After one minute intervals, the procedure was repeated with a second and third 10 ml insult.

The acquisition rate from each fluid insult was determined according to the following formula:

$$\text{Acquisition Rate (ml/s)} = \frac{\text{volume of fluid insult (ml)}}{\text{acquisition time (s)}}$$

The composite materials described above were also subjected to fluid retention testing by measuring the amount of 0.9% saline solution that could be absorbed back through the top sheet of the structure by a stack of filter paper under 0.1 psi pressure after each fluid insult. Samples for 3 separate measurements (each measuring 8½"×11 ") were prepared. Each sample was placed onto a plastic platform with tissue side down and its center was marked. 10 ml of 0.9% saline solution (first insult) was drained onto the sample from a funnel from a distance of approximately 1.5" above the center of the sample. The sample was allowed to sit for 20 minutes. A stack of 12 filter papers was weighed and placed on the center of the wetted area and pressed by a circular weight on top. After 2 minutes the wet filter papers were removed and weighed again. This procedure was repeated with a second insult of 10 ml saline and a stack of 16 filter papers, and a third insult of 10 ml saline and a stack of 20 filter papers. The rewet value and the percent fluid retention was calculated for the first, second and third insults according to the following formulas:

$\text{Rewet}_{1, 2 \text{ or } 3}$ = Wet filter papers weight−Dry filter papers weight %
Retention = (50−Rewet)50×100%

Further, the size of the fluid stain after the third insult on the fluid retention test was recorded. The results are shown in Table 4.

TABLE 4

Acquisition Rate and Fluid Retention Testing

| Sample | Acquisition Rate (ml/sec) | | | Fluid Retention (%) | | | Stain Area |
|---|---|---|---|---|---|---|---|
|  | $1^{st}$ Insult | $2^{nd}$ Insult | $3^{rd}$ Insult | $1^{st}$ Insult | $2^{nd}$ Insult | $3^{rd}$ Insult | Sq. cm. |
| Example 1 - MJ998-MF-17 | 3.7 | 1.6 | 1.4 | 99% | 97% | 86% | 112 |
| Example 2 - MJ998-MF-18b | 7.5 | 6.1 | 4.9 | 99% | 91% | 73% | 79 |
| Example 3 - MJ998-MF-9 | 5.4 | 3.5 | 2.9 | 98% | 79% | 55% | 95 |

A comparison of MF-9 and MF-17 shows that moving the fluid distribution stratum from the middle position (as in MNF-9) to the bottom of the three stratum structure (as in MF 17) significantly increases the fluid retention at the expense of some reduction of fluid acquisition rate and increase in fluid stain size.

The double compaction embodiment of the present invention, MF-18b, shows improvement over MF-9 for fluid acquisition rate, fluid retention, and stain size.

Additional Examples

In the following examples, the raw materials are, unless otherwise noted, the following:

| | |
|---|---|
| Standard Fluff Pulp: | Foley Fluff (Buckeye Technologies Inc., Memphis, TN) |
| Resilient Fluff Pulp: | HPF (Buckeye Technologies Inc., Memphis, TN) |
| Compressible Fluff Pulp: | ND416 (Weyerhaeuser-Tacoma, WA) |
| Superabsorbent Powder: | 1180 (Stockhausen-Greensboro, NC) |
| Binder Fiber: | T-255, 2.8 dtex X 4 mm (Kosa, Charlotte, NC) |
| PET Fiber: | T-224, 17 dtex X 6 mm (Kosa, Charlotte, NC) |
| Latex Binder: | AirFlex 192 (Air Products, Allentown, PA) |

The composite materials described above were subjected to a fluid acquisition test and a fluid retention test as described above, unless otherwise noted.

Examples 4 and 5
Acquisition Stratum Matrix Fibers

Examples 4 and 5 compare latex bonded fluff cellulose fibers with latex bonded synthetic fibers in the acquisition stratum of a composite absorbent structure.

Example BU124-19 is an embodiment of the invention with a latex bonded PET fiber acquisition stratum and BU124-22 is identical to BU124-19 except that the acquisition stratum is comprised of latex bonded standard fluff cellulose fibers.

TABLE A1

Absorbent Structure with Latex Binder in the Acquisition Stratum - Example BU12422

| | Distribution Stratum Bottom (g/m²) | Storage Stratum Middle (g/m²) | Acquisition Stratum Top (g/m²) | Sum (g/m²) | Total |
|---|---|---|---|---|---|
| Compressible Pulp | 69.3 | 0.0 | 0.0 | 69.3 | 18.8% |
| Resilient Pulp | 0.0 | 43.7 | 0.0 | 43.7 | 27.0% |
| SAP Powder | 0.0 | 55.9 | 0.0 | 55.9 | 23.0% |
| Binder Fiber | 6.2 | 7.6 | 0.0 | 13.8 | 6.4% |
| PET Fiber | 0.0 | 0.0 | 0.0 | 0.0 | 0.0% |
| Standard Fluff Pulp | 0.0 | 0.0 | 38.4 | 38.4 | 15.8% |
| Latex Binder | 0.0 | 0.0 | 6.8 | 6.8 | 2.8% |
| Carrier Tissue | 15.0 | 0.0 | 0.0 | 15.0 | 6.2% |
| Total | 90.5 | 107.2 | 45.2 | 242.9 | 100.0% |

TABLE A2

Absorbent Structure with Latex Binder in the Acquisition Stratum - Example BU124-19

| | Distribution Stratum Bottom (g/m²) | Storage Stratum Middle (g/m²) | Acquisition Stratum Top (g/m²) | Sum (g/m²) | Total |
|---|---|---|---|---|---|
| Compressible Pulp | 69.3 | 0.0 | 0.0 | 69.3 | 18.8% |
| Resilient Pulp | 0.0 | 43.7 | 0.0 | 43.7 | 27.0% |
| SAP Powder | 0.0 | 55.9 | 0.0 | 55.9 | 23.0% |
| Binder Fiber | 6.2 | 7.6 | 0.0 | 13.9 | 6.4% |
| PET Fiber | 0.0 | 0.0 | 38.4 | 38.4 | 0.0% |
| Standard Fluff Pulp | 0.0 | 0.0 | 0.0 | 0.0 | 15.8% |
| Latex Binder | 0.0 | 0.0 | 6.8 | 6.8 | 2.8% |
| Carrier Tissue | 15.0 | 0.0 | 0.0 | 15.0 | 6.2% |
| Total | 90.5 | 107.2 | 45.2 | 243 | 100.0% |

Table A3 shows the relative fluid acquisition and retention performance of samples BU124-22 (having a latex bonded standard cellulose fluff acquisition stratum) and BU124-19 (having a latex bonded PET fiber acquisition stratum).

TABLE A3

Relative Performance of Absorbent Structures BU124-22 and BU124-19 with Latex Binder in the Acquisition Stratum

| | Fluid Retention - 7 ml Insults | | | Acquisition Rate 3rd 5 ml Insult |
|---|---|---|---|---|
| Grade | 1st insult | 2nd Insult | 3rd Insult | (ml/sec) |
| BU124-22 | 74.1% | 52.8% | 38.1% | 0.053 |
| BU124-19 | 95.6% | 71.5% | 56.1% | 0.18 |

Examples 6 and 7

SAP in Middle Stratum vs. SAP in Bottom Stratum of a Three Stratum Unitary Structure.

Examples 6 and 7 compare absorbent structures with SAP in the middle stratum versus absorbent structures with SAP in the bottom stratum of a three stratum unitary structure.

Example X575 is a preferred embodiment of the invention with the SAP in the middle stratum; example X572 is similar to X575 except that the superabsorbent powder is placed in the bottom stratum.

TABLE B1

Absorbent Structure with SAP in Middle Stratum - Example X575

| | Distribution Stratum Bottom (g/m²) | Storage Stratum Middle (g/m²) | Acquisition Stratum Top (g/m²) | Sum (g/m²) | Total |
|---|---|---|---|---|---|
| Compressible Pulp | 69.3 | 0.0 | 0.0 | 69.3 | 18.8% |
| Resilient Pulp | 0.0 | 43.7 | 0.0 | 43.7 | 27.0% |
| SAP Powder | 0.0 | 55.9 | 0.0 | 55.9 | 23.0% |
| Binder Fiber | 6.2 | 7.6 | 0.0 | 13.9 | 6.4% |
| PET Fiber | 0.0 | 0.0 | 38.4 | 38.4 | 15.8% |
| Latex Binder | 0.0 | 0.0 | 6.8 | 6.8 | 2.8% |
| Carrier Tissue | 15.0 | 0.0 | 0.0 | 15.0 | 6.2% |
| Total | 90.5 | 107.2 | 45.2 | 243 | 100.0% |
| Density | 0.133 gr/cc | | | | |

TABLE B2

Absorbent Structure with SAP in Bottom Stratum - Example X572

| | Storage Stratum Bottom (g/m²) | Distribution Stratum Middle (g/m²) | Acquisition Stratum Top (g/m²) | Sum (g/m²) | Total |
|---|---|---|---|---|---|
| Compressible Pulp | 45.8 | 0.0 | 0.0 | 45.8 | 18.g% |
| Resilient Pulp | 0.0 | 65.6 | 0.0 | 65.6 | 27.0% |
| SAP Powder | 55.9 | 0.0 | 0.0 | 55.9 | 23.0% |
| Binder Fiber | 7.6 | 7.9 | 0.0 | 15.6 | 6.4% |
| PET Fiber | 0.0 | 0.0 | 38.4 | 38.4 | 15.8% |
| Latex Binder | 0.0 | 0.0 | 6.8 | 6.8 | 2.8% |
| Carrier Tissue | 15.0 | 0.0 | 0.0 | 15.0 | 6.2% |
| Total | 124.3 | 73.5 | 45.2 | 243.1 | 100.0% |
| Density | 0.114 gr/cc | | | | |

Table B3 shows the fluid acquisition and retention performance of samples X575 and X572.

TABLE B3

Relative Performance of Absorbent Structures with SAP in Bottom (X572) and Middle (X575) Strata and

| | Fluid Retention - 7 ml Insults | | | Acquisition Rate 3rd 5 ml Insult |
|---|---|---|---|---|
| Sample | 1st insult | 2nd Insult | 3rd Insult | (ml/sec) |
| X572 | 99.1% | 72.3% | 48.1% | 0.171 |
| X575 | 99.0% | 90.4% | 66.6% | 0.255 |

Examples 8 and 9
Preferred Embodiments vs. Commercial Thin Sanitary Pads

Examples 8 and 9 compare several preferred absorbent structures of this application with commercial thin sanitary pads.

Examples X573 and X574 are preferred embodiments of the invention. They differ from sample X575 only in basis weight.

TABLE C1

3 Strata Absorbent Structure - Example X573

| | Distribution Stratum Bottom (g/m$^2$) | Storage Stratum Middle (g/m$^2$) | Acquisition Stratum Top (g/m$^2$) | Sum (g/m$^2$) | Total |
|---|---|---|---|---|---|
| Compressible Pulp | 45.5 | 0.0 | 0.0 | 45.5 | 26.0% |
| Resilient Pulp | 0.0 | 31.5 | 0.0 | 31.5 | 18.0% |
| SAP Powder | 0.0 | 40.3 | 0.0 | 40.3 | 23.0% |
| Binder Fiber | 4.5 | 5.5 | 0.0 | 10.0 | 5.7% |
| PET Fiber | 0.0 | 0.0 | 27.7 | 27.7 | 15.8% |
| Latex Binder | 0.0 | 0.0 | 4.9 | 4.9 | 2.8% |
| Carrier Tissue | 15.0 | 0.0 | 0.0 | 15.0 | 8.6% |
| Total | 65.0 | 77.3 | 32.6 | 174.9 | 100% |
| Density | 0.105 gr/cc | | | | |

TABLE C2

3 Strata Absorbent Structure - Example X574

| | Distribution Stratum Bottom (g/m$^2$) | Storage Stratum Middle (g/m$^2$) | Acquisition Stratum Top (g/m$^2$) | Sum (g/m$^2$) | Total |
|---|---|---|---|---|---|
| Compressible Pulp | 59.6 | 0.0 | 0.0 | 59.6 | 27.777 |
| Resilient Pulp | 0.0 | 38.7 | 0.0 | 38.7 | 18.0% |
| SAP Powder | 0.0 | 49.5 | 0.0 | 49.5 | 23.0% |
| Binder Fiber | 5.5 | 6.7 | 0.0 | 12.3 | 5.7% |
| PET Fiber | 0.0 | 0.0 | 34.0 | 34.0 | 15.8% |
| Latex Binder | 0.0 | 0.0 | 6.0 | 6.0 | 2.8% |
| Carrier Tissue | 15.0 | 0.0 | 0.0 | 15.0 | 7.0% |
| Total | 80.1 | 94.9 | 40.0 | 215.1 | 100.0% |
| Density | 0.124 gr/cc | | | | |

Table C3 shows the fluid acquisition and retention performance of preferred embodiments of the invention vs. commercially available thin sanitary pads.

TABLE C3

Relative Performance of Examples X573, X574, X575, and Commercial Thin Sanitary Pads

| Sample | Basis Weight (gsm) | Fluid Retention - 7 ml Insults | | | Acquisition Rate 3rd 5 ml Insult (ml/sec) |
|---|---|---|---|---|---|
| | | 1st Insult | 2nd Insult | 3rd Insult | |
| X573 | 170 | 95.6% | 62.7% | 42.4% | 0.164 |
| X574 | 215 | 98.9% | 79.4% | 57.1% | 0.195 |
| X575 | 243 | 99.0% | 90.4% | 66.6% | 0.255 |
| Brand | | | | | |
| A | 368 | 80.0% | 58.6% | 44.3% | 0.040 |
| B | 233 | 87.1% | 68.6% | 51.4% | 0.068 |
| C | 250 | 81.4% | 58.6% | 38.6% | 0.018 |

Examples 10 and 11
Chemically Modified Fluff Cellulose vs. Standard Fluff Cellulose Examples 10 and 11 compare structures including chemically modified fluff cellulose and standard fluff cellulose for the storage stratum.

TABLE D1

Absorbent Structure with Standard Fluff Cellulose - Example MJ299-MF-2

| | Distribution Stratum Bottom (g/m$^2$) | Storage Stratum Middle (g/m$^2$) | Acquisition Stratum Top (g/m$^2$) | Sum | Total |
|---|---|---|---|---|---|
| Compressible Pulp | 61.8 | 0.0 | 0.0 | 61.8 | 28.2% |
| Resilient Pulp | 0.0 | 0.0 | 0.0 | 0.0 | 27.0% |
| Standard Pulp | 0.0 | 55.0 | 0.0 | 55.0 | 27.0% |
| SAP Powder | 0.0 | 40.0 | 0.0 | 40.0 | 23.0% |
| Binder Fiber | 3.3 | 5.0 | 0.0 | 8.3 | 6.4% |
| PET Fiber | 0.0 | 0.0 | 34.0 | 34.0 | 15.8% |
| Latex Binder | 0.0 | 0.0 | 6.0 | 6.0 | 2.8% |
| Carrier Tissue | 15.0 | 0.0 | 0.0 | 15.0 | 6.2% |
| Total | 80.1 | 100.0 | 40.0 | 220.1 | 100.0% |
| Density | 0.127 gr/cc | | | | |

TABLE D2

Absorbent Structure with Resilient Cellulose Pulp - Example MJ299-MF-6

| | Distribution Stratum Bottom (g/m$^2$) | Storage Stratum Middle (g/m$^2$) | Acquisition Stratum Top (g/m$^2$) | Sum (g/m$^2$) | Total |
|---|---|---|---|---|---|
| Compressible Pulp | 61.8 | 0.0 | 0.0 | 61.8 | 28.1% |
| Resilient Pulp | 0.0 | 55.0 | 0.0 | 55.0 | 27.0% |
| Standard Pulp | 0.0 | 0.0 | 0.0 | 0.0 | 27.0% |
| SAP Powder | 0.0 | 40.0 | 0.0 | 40.0 | 23.0% |
| Binder Fiber | 3.3 | 5.0 | 0.0 | 8.3 | 6.4% |
| PET Fiber | 0.0 | 0.0 | 34.0 | 34.0 | 15.8% |
| Latex Binder | 0.0 | 0.0 | 6.0 | 6.0 | 2.8% |
| Carrier Tissue | 15.0 | 0.0 | 0.0 | 5.0 | 6.2% |
| Total | 80.1 | 100.0 | 40.0 | 220.1 | 100.0% |
| Density | 0.126 g/cc | | | | |

Table D3 gives the fluid acquisition and retention performance for samples MJ299-MF-2 and MJ299-MF-6. The test procedure used for Table D3 deviates for the MQ3RlD023 fluid acquisition and MQ3RD022 fluid retention procedures in that multiple 10 ml insults of 0.9% saline solution are utilized in both the fluid acquisition and retention tests.

TABLE D3

Relative Performance of Absorbent Structure with Standard Fluff Cellulose (MJ299-MF-2) and Resilient Cellulose Pulp (MJ299-MF-6)

| Grade | Fluid Retention - 7 ml Insults | | | Acquisition Rate 3rd 5 ml Insult (ml/sec) |
|---|---|---|---|---|
|  | 1st Insult | 2nd Insult | 3rd Insult |  |
| MJ299-MF-2 | 9:8.6% | 76.6% | 42.8% | 0.9 |
| MJ299-MF-6 | 98.8% | 73.9% | 72.0% | 1.5 |

Example 12

Preferred Embodiment vs. Commercial Infant Diapers

Example 12 compares several preferred absorbent structures of this application with commercially available infant diapers.

TABLE E1

Absorbent Structure Suitable for Use in Diapers - Example MJ998-HMF-3

|  | Distribution Stratum Bottom (g/m²) | Storage Stratum Middle (g/m²) | Acquisition Stratum Top (g/m²) | Sum (g/m²) | Total |
|---|---|---|---|---|---|
| Compressible Pulp | 95.0 | 0.0 | 0.0 | 95.0 | 20.4% |
| Resilient Pulp | 0.0 | 0.0 | 0.0 | 0.0 | 0.0% |
| Standard Pulp | 0.0 | 105.0 | 0.0 | 105.0 | 22.6% |
| SAP Powder | 0.0 | 180.0 | 0.0 | 180.0 | 38.7% |
| Binder Fiber | 5.0 | 15.0 | 0.0 | 20.0 | 4.3% |
| PET Fiber | 0.0 | 0.0 | 42.5 | 42.5 | 9.1% |
| Latex Binder | 0.0 | 0.0 | 8.0 | 8.0 | 1.7% |
| Carrier Tissue | 15.0 | 0.0 | 0.0 | 15.0 | 3.2% |
| Total | 115.0 | 300.0 | 50.5 | 465.5 | 100.0% |
| Density | 0.122 gr/cc |  |  |  |  |

Table E2 shows the fluid acquisition rate and fluid retention test results for sample MJ998-HMF-3 and several commercially available diapers. The test procedures are similar to the other examples except that all fluid insults are 50 ml of 0.9% saline and that the MJ998-NHF-3 was cut into a 10 cm×25 cm section.

TABLE E2

Performance of Example MJ998-HMF-3

|  |  | Multiple 50 ml Saline Insults | | | |
|---|---|---|---|---|---|
| Sample | Basis Weight (gsm) | Fluid Retention (%) | | | Acquisition Rate (ml/sec) |
|  |  | 1st Insult | 2nd Insult | 3rd Insult | 3rd Insult |
| MJ998-HMF-3 | 477 | 99.9% | 99.8% | 99.5% | 3.7 |
| Commercial D | 622 | 99.9% | 96.8% | 79.8% | 2.4 |
| Commercial E | 792 | 99.9% | 99.0% | 95.9% | 1.8 |
| Commercial F | 522 | 99.5% | 96.9% | 87.3% | 2.9 |
| Commercial G | 840 | 96.4% | 79.1% | 57.2% | 2.5 |

Example 13

TABLE F

| Compressive Force | PET | HPF | Foley Fluff | ND-416 |
|---|---|---|---|---|
| 0 PSI | 0.070 | 0.032 | 0.032 | 0.038 |
| 450 PSI | 0.094 | 0.099 | 0.100 | 0.113 |
| 900 PSI | 0.100 | 0.117 | 0.126 | 0.170 |
| 1350 PSI | 0.105 | 0.133 | 9.161 | 0.198 |

Table F provides a comparison of the response of various fluff cellulose fibers and a PET fiber to a given compressive force. The fibers in Table F are: 15 denier×6 mm×4 crimps/inch PET fiber from Kosa (Salisbury, N.C.); HPF, a chemically stiffened fluff cellulose fiber from Buckeye Technologies; Foley Fluff, a standard fluff cellulose fiber from Buckeye Technologies; ND-416, a chemically softened fluff cellulose fiber from Weyerhaeuser (Tacoma, Wash.).

A blend containing a 90 gsm sample of each fiber with 10 gsm of a T-255 binder fiber was opened and air formed into a 100 gsm fiber batt. The fiber batt was bonded in a hot air oven. Separate pieces of each of the materials were subjected to a compressive force of 0 psi, 450 psi, 900 psi and 1350 psi for a period of one minute. The caliper of each compressed sample was measured to determine the density. The density as a function of compressive force is shown in Table F. This tabulation shows that the various fibers will yield a bonded air laid material with a density dependent upon the compressive force applied.

Thus, a compressed unitary structure with a top stratum comprised of PET fibers, and middle stratum comprising Buckeye HPF fibers and a bottom stratum comprised of Weyerhaeuser ND-416 fibers will not have a constant density from top to bottom. Instead, The data shown in Table F shows that a three-tier density gradient will occur in the compressed structure with the top PET stratum having the lowest density and the bottom ND-416 stratum having the highest density.

What is claimed is:

1. A unitary absorbent structure comprising:
    a. a fluid acquisition stratum having a basis weight of from 20 to 120 gsm comprising synthetic fibers and a binder;
    b. a fluid distribution stratum having a basis weight of from 20 to 200 gsm comprising cellulose fibers and a binder; and
    c. a fluid storage stratum between the acquisition stratum and the distribution stratum, having a basis weight of from 60 to 400 gsm, wherein the acquisition stratum is coextensively contiguous with and in direct fluid communication with the storage stratum, the storage stratum is coextensively contiguous with and in direct fluid communication with the distribution stratum, the acquisition stratum and the distribution stratum are in indirect fluid communication, and the average pore size of each stratum decreases in a gradient in the direction from the acquisition stratum to the distribution stratum.

2. The unitary absorbent structure of claim 1, wherein (a) the fluid acquisition stratum comprises polyester fibers; and (b) the fluid storage stratum includes 10 to 75% by weight superabsorbent polymer.

3. The unitary absorbent structure of claim 1, wherein the average resiliency of each stratum decreases in a gradient in the direction from the acquisition stratum to the distribution stratum.

4. The unitary absorbent structure of claim 1, wherein the acquisition stratum contains an aqueous latex binder resin, bicomponent fibers or a mixture thereof.

5. The unitary absorbent structure of claim 1, wherein the binder in the acquisition stratum is latex.

6. The unitary absorbent structure of claim 1, wherein the binder in the acquisition stratum is selected from the group consisting of bicomponent fibers, polyolefin powder, and mixtures thereof.

7. The unitary absorbent structure of claim 1, wherein the acquisition stratum comprises polyester terephthalate (PET) fiber that is at least 2 denier in size.

8. The unitary absorbent structure of claim 1, wherein the acquisition stratum comprises 3–15 denier crimped PET fiber with a cut length of between about 3 and about 12 mm.

9. The unitary absorbent structure of claim 1, wherein the acquisition stratum comprises a first substratum comprising cellulosic fibers and a second substratum comprising synthetic fibers, and wherein the first substratum is closer than the second substratum to the storage stratum.

10. The unitary absorbent structure of claim 1, wherein the storage and distribution stratums each contain thermoplastic bonding fibers.

11. The unitary absorbent structure of claim 1, wherein the storage stratum comprises cellulosic fibers and superabsorbent polymer.

12. The unitary absorbent structure of claim 1, wherein the storage stratum comprises cellulosic fibers that have been modified to increase the curl and/or stiffness of the fibers.

13. The unitary absorbent structure of claim 1, wherein the average pore size of the distribution stratum is less than the average pore size of either the acquisition or storage strata.

14. The unitary absorbent structure of claim 1, wherein the average pore size of the distribution stratum is less than one half the average pore size of the acquisition and storage strata.

15. The unitary absorbent structure of claim 1, wherein the distribution stratum comprises cellulosic fibers that have been modified to decrease the stiffness of the fibers.

16. The unitary absorbent structure of claim 1, further comprising a tissue layer in contact with the surface of the distribution stratum that faces opposite to the storage stratum.

17. A diaper incorporating the unitary absorbent structure of claim 1.

18. A feminine hygiene pad incorporating the unitary absorbent structure of claim 1.

19. An adult incontinence pad incorporating the unitary absorbent structure of claim 1.

* * * * *